United States Patent [19]

Kokusho et al.

[11] Patent Number: 4,624,919

[45] Date of Patent: Nov. 25, 1986

[54] ENZYMATIC PRODUCTION OF PHOSPHOLIPID-SACCHARIDE DERIVATIVES

[75] Inventors: Yoshitaka Kokusho, Kunitachi; Shigeaki Kato; Haruo Machida, both of Hino, all of Japan

[73] Assignee: Meito Sangyo Kabushiki Kaisha, Aichi, Japan

[21] Appl. No.: 598,699

[22] Filed: Apr. 10, 1984

[30] Foreign Application Priority Data

Apr. 11, 1983 [JP] Japan .................................. 58-63306

[51] Int. Cl.$^4$ .......................... C12P 19/00; C12P 9/00; C07H 11/04
[52] U.S. Cl. .......................... 435/74; 435/72; 435/131; 536/4.1; 536/17.1; 536/55.2; 536/117
[58] Field of Search ................. 536/117, 17.1; 435/72, 435/74, 131

[56] References Cited

U.S. PATENT DOCUMENTS 2,052,029 8/1936 Harris .................................. 536/117
3,142,620 7/1964 Bloch .................................. 536/18.2

FOREIGN PATENT DOCUMENTS 1581810 4/1978 United Kingdom .

OTHER PUBLICATIONS

Nojima, "The Jour. of Biochemistry", vol. 46, No. 5, 1959, pp. 607–620.
M. Kates, "Lecithinase Systems in Sugar Beet, Spinach, Cabbage and Carrot", Can. J. Biochem. Physiol., 32 (1954), pp. 571–583.
R. M. C. Dawson, "The Formation of Phosphatidylglycerol and Other Phospholipids by the Transferase Activity of Phospholipase D", Biochm. J., 102, (1967) 205–210.
S. F. Yang, "Transphosphatidylation by Phospholipase D", J. Biol. Chem., 242, (1967), 477–484.

Primary Examiner—Johnnie R. Brown
Attorney, Agent, or Firm—Sherman and Shalloway

[57] ABSTRACT

A process for producing a saccharide derivative of a phospholipid, which comprises reacting a phospholipid with a monosaccharide having 5 to 7 carbon atoms, at least one primary alcohol group and at least three hydroxyl groups in total including the OH of the primary alcohol group or a disaccharide thereof, said saccharide being optionally substituted by a group selected from the class consisting of amino and acetylamino groups, or a phenol glycoside of said saccharide in the presence of phospholipase DM. The phospholipid-saccharide derivatives are useful as a liposome-forming substrate, or as an emulsifier for cosmetics, such as cream and lotion, fat solutions for transfusion and agricultural chemicals, such as pesticides and herbicides.

15 Claims, No Drawings

ENZYMATIC PRODUCTION OF PHOSPHOLIPID-SACCHARIDE DERIVATIVES

This invention relates to phospholipid-saccharide derivatives, and a process for production thereof by an enzymatic technique.

The process of this invention can produce a wide range of phospholipid-saccharide derivatives including those which have heretofore been considered impossible of production by an enzymatic technique.

Particularly, this invention relates to a process for producing a saccharide derivative of a phospholipid, which comprises reacting a phospholipid with a saccharider or its phenol glycoside in the presence of phospholipase DM having an optimum temperature of 60° to 70° C. and an optimum pH of about 7 which differs from cabbage-derived phospholipase D (optimum temperature not more than 40° C., optimum pH 5.4–5.6) previously used in the enzymatic technique; and to the resulting phospholipid-saccharide derivative.

In the present invention, the term "saccharide derivative of a phospholipid" denotes a new phospholipid which is different from the starting phospholipid and obtained by hydrolyzing the ester linkage between the phosphoric acid structural moiety of the starting phospholipid and its alcohol structural moiety by the action of phospholipase DM and simultaneously transferring the phospholidic acid structural moiety to the saccharide or its phenol glycoside used in the reaction.

More specifically, the present invention relates to a process for producing a saccharide derivative of a phospholipid, which comprises reacting a phospholipid represented by the following formula $$A-O-\overset{\overset{O}{\|}}{\underset{OH}{P}}-O-B$$

wherein

A is a moiety represented by the following formula (i)

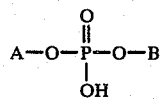

in which $R_1$ and $R_2$ both represent $-O-COR_{11}$ or $-O-R_{12}$, or $R_1$ and $R_2$ in formula (i) together represent

in which n represents a number of from 11 to 19, and $R_{11}$ and $R_{12}$ are identical or different and each represents a saturated or unsaturated aliphatic hydrocarbon group having 7 to 21 carbon atoms, and B represents the group $-CH_2)_2N^+(CH_3)_3$, $-CH_2)_2NH_2$, $-CH_2CH(NH_2)COOH$, $-CH_2CH_2NH(CH_3)$, $-CH_2CH_2N(CH_3)_2$, $-CH_2CHOHCH_2OH$ or $-CH_2)_mH$ in which m represents a number of from 1 to 5, with a monosaccharide having 5 to 7 carbon atoms, at least one primary alcohol group and at least three hydroxyl groups in total including the OH of the primary alcohol group or disaccharide thereof, said saccharide being unsubstituted or substituted by a group selected from the class consisting of amino and acetylamino groups, or a phenol glycoside of said saccharide in the presence of phospholipase DM; and to the resulting phospholipid-saccharide derivative.

It has previously been known that phospholipase D catalyzes reaction of hydrolyzing the choline base-phosphoric acid ester of a phospholipid such as phosphatidyl choline to form a free base and phosphatidic acid [M. Kates: Can. J. Biochem. Physiol., 32, 571 (1954)].

It was reported that when a phospholipid such as lecithin is reacted with ethanol in the presence of phospholipase D, the ester linkage between the phosphatidic acid structural moiety and the alcohol structural moiety of the phospholipid is hydrolyzed, and simultaneously by the action of the enzyme to transfer the phosphatidyl group, phosphatidyl ethanol is formed [R. M. C. Dawson: Biochem. J., 102, 205, (1967); and S. F. Yang: J. Biol. Chem., 242, 477 (1967)].

Since the action of phospholipase D to transfer the phosphatidyl group became known, research work in this field has been undertaken. For example, one result of such work is disclosed in British Pat. No. 1,581,810 (corresponding to West German OLS No. 2717547). This patent document describes a primary alcohol transfer reaction between a phospholipid represented by the general formula in this patent document and a primary alcohol having a linear or branched alkyl group having up to 5 carbon atoms and optionally substituted by a hydroxyl group, halogen, an amino group, etc., utilizing the enzymatic action of the aforesaid cabbage-derived phospholipase D. The patent document states that this reaction takes place only with primary alcohols having up to 5 carbon atoms, and with primary alcohols having more than 5 carbon atoms, the main reaction product is the corresponding phosphatidic acid. This patent document also states that the selection of the alcohol component is not particularly limited so long as it is the primary alcohol meeting the above requirement. It, however, fails to describe or suggest anything about the reaction of the phospholipid with a saccharide or its phenol glycoside.

R. M. C. Dawson reported that lecithin as a phospholipid was reacted respectively with sucrose, glucose and galactose as saccharides in the presence of the known cabbage-derived phospholipase D, but the transfer of the phosphatidyl group of the lecithin substrate to these saccharides did not take place [Biochem. J., vol. 102, 205–209 (1967)].

S. F. Yang reported that as a result of the same experiment as above with glucose and inositol, transfer to saccharides did not occur [J. Biol. Chem., vol. 242, 477–484 (1967)].

It has been technical common knowledge therefore that a transfer reaction between a phospholipid and an alcohol in the presence of the conventional phospholipase D occurs only with primary alcohols, particularly primary alcohols having a relatively small number of carbon atoms, and not with saccharides.

The present inventors discovered the existence of microorganisms having the ability to produce phospholipase D which differ from the known phospholipase D in optimum temperature, optimum pH, etc., and disclosed them in Japanese Patent Application No.

161076/1981 (Japanese Laid-Open Patent Publication No. 63388/1983 laid open on Apr. 15, 1983) and Japanese Patent Publication No. 163475/1981 (Japanese Laid-Open Patent Publication No. 67183/1983 laid open on Apr. 21, 1983).

Further investigations have led to the surprising discovery that while the enzymes produced by the aforesaid phospholipase-producing microorganisms (to be referred to in this invention as phospholipases DM) have previously been considered incapable of catalyzing the formation of phospholipid-saccharide derivatives, they show an enzymatic catalytic action which makes possible the performance of a transfer reaction between a broad range of phospholipids and saccharides or the phenol glycosides thereof.

The present inventors' investigations have led to the surprising discovery that there exists an enzyme newly called phospholipase DM in the present invention which catalyzes the formation of a phospholipid-saccharide derivative from a phospholipid and a saccharide such as fructose, and by reacting the phospholipid with the mono- or di-saccharide or its phenol glycoside in the presence of the phospholipase DM, new derivatives including phospholipid-saccharide derivatives previously considered impossible of formation can be obtained.

The present inventors' investigations have shown that phospholipid-saccharide derivatives can be produced in good yields by an enzymatic technique under mild conditions by using easy means without the need for complex and disadvantageous chemical synthesizing means and without a likelihood of side reactions.

It is an object of this invention to provide new enzyme method phospholipid derivatives and a process for production thereof.

The above and other objects and advantages of this invention will become more apparent from the following description.

The starting phospholipid utilized in the process of this invention is represented by the following general formula.

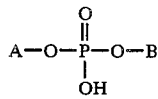

wherein

A is a moiety represented by the following formula (i)

in which $R_1$ and $R_2$ both represent $-O-COR_{11}$ or $-O-R_{12}$, or $R_1$ and $R_2$ in formula (i) together represent

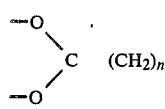

in which n represents a number of from 11 to 19, and $R_{11}$ and $R_{12}$ are identical or different and each represents a saturated or unsaturated aliphatic hydrocarbon group having 7 to 21 carbon atoms, and B represents the group $-(CH_2)_2N^+(CH_3)_3$, $-(CH_2)_2NH_2$, $-CH_2CH(NH_2)COOH$, $-CH_2CH_2NH(CH_3)$, $-CH_2CH_2N(CH_3)_2$, $-CH_2CHOHCH_2OH$ or $-(CH_2)_mH$ in which m represents a number of from 1 to 5.

The starting phospholipids of the above formula are known compounds and are available on the market. They can be extracted from naturally occurring materials, or synthesized, by methods known per se. For example, lecithin, cephalin, phosphatidyl serine, phosphatidyl-N-methylethanolamine, phosphatidyl N,N-dimethylethanolamine, phosphatidyl glycerol, and alkyl esters of phosphatidic acid which can be obtained by extraction from animal and vegetable tissues by known means, either singly or in mixture, can be used directly or after purification. Alkyl ether-type phospholipids or beta-type phospholipids can also be utilized by chemically synthesizing a part or the whole of their structures by known methods.

The saccharide or its phenol glycoside to be reacted with the starting phospholipid in the presence of phospholipase DM in the process of this invention is a monosaccharide having 5 to 7 carbon atoms, at least one primary alcohol group, and in total at least three hydroxyl groups, or a disaccharide thereof. The saccharide may be substituted by an amino group or an acetylamino group. Specific examples of the saccharide or its phenol glycoside include pentoses such as D- and L-arabinoses, D-ribose, 2-deoxy-D-ribose, D-lyxose, D-xylose, D- and L-ribuloses, D- and L-xyluloses, alpha- or beta-methyl-xyloside, beta-methyl-arabinoside, 2-O-methyl-xylose, beta-methyl-riboside; hexoses such as 2-deoxy-D-glucose, D-glucose, D-galactose, D-mannose, L-sorbose, D-talose, D-fructose, alpha- or beta-methyl-galactoside, alpha- or beta-methyl-glucoside, alpha- or beta-methyl mannoside, and 3-O-methyl-glucose; heptoses such as D-alpha-glucoheptose and sedoheptulose; amino sugars such as D-galactosamine, D-glucosamine, D-mannosamine, N-acetyl-D-galactosamine, N-acetyl-D-glucosamine and N-acetyl-D-mannosamine; phenol glycosides such as salicin, arbutin, 1-o-phenyl-alpha- or beta-D-glucoside and 1-o-phenyl-alpha- or beta-D-galactoside; and disaccharides such as saccharose, maltose, cellobiose, gentiobiose, lactose, melibiose, isomaltose, and N,N'-diacetyl-chitobiose.

The above-exemplified saccharides or their phenol glycosides may be naturally occurring materials or synthetic products. Preferably, they are used after they have been purified by utilizing suitable known means in order to avoid inclusion of the undesired saccharides or their phenol glycosides. The purification means include, for example, column chromatography on cellulose, silica gel, alumina, activated carbon and various ion exchange resins, gel filtration using Sephadex, and suitable combinations of these.

According to this invention, the phospholipid is reacted with the saccharide or its phenol glycoside in the presence of phospholipase DM.

The phospholipase DM used at this time may, for example, be a phospholipase DM which is produced by a phospholipase DM-producing microorganism. The phospholipase DM can be distinguished from the known phospholipase D extracted from cabbage in that the latter has an optimum temperature of not more than 40° C. and an optimum pH of 5.4 to 5.6, whereas the former has an optimum temperature of 60° to 70° C. and an optimum pH of about 7. The phospholipase DM can also be distinguished from the known phospholipase D in that the former catalyzes the formation of a phospholipid-saccharide derivative from fructose and lecithin as the phospholipid.

Examples of the phospholipase DM-producing microorganism are those belonging to the genus Nocardiopsis, such as Nocardiopsis sp. No. 779 (FERM-P No. 6133; the international deposit number BP 512 under the Budapest Treaty), disclosed in the above-cited Japanese Patent Application No. 161076/1981 (Laid-Open Patent Publication No. 63388/1983 laid open on Apr. 15, 1983), and those belonging to the genus Actinomadura, such as Actinomadura sp. No. 362 (FERM-P No. 6132; the international deposit number BP 511 under the Budapest Treaty) which are disclosed in Japanese Patent Publication No. 163475/1981 (Laid-Open Patent Publication No. 67183/1983 laid open on Apr. 21, 1983). Table 1 below summarizes the differences in enzymological properties between the phospholipases DM used in the process of this invention and the known phospholipase D.

TABLE 1

|  | Phospholipase DM from the Actinomadura strain | Phospholipase DM from the Nocardiopsis strain | Known phospholipase D from cabbage |
|---|---|---|---|
| Optimum temperature (°C.) | 60-70 | 60-70 | below 40 |
| Optimum pH | About 7 | About 7 | 5.4-5.6 |
| Activators | Nonionic surfactants such as Triton X-100, deoxycholic acid Cholic acid, $Ca^{++}$, diethyl ether, and albumin | Nonionic surfactants such as Triton X-100, diethyl ether, and $Ca^{++}$ | Anionic surfactants such as sodium dodecylsulfate, deoxycholic acid, phosphatidic acid, $Ca^{++}$, diethyl ether |
| Inhibitors | Cetyl pyridinium chloride | Sodium dodecylsulfate, and cetyl pyridinium chloride | EDTA, cationic surfactants, choline, ethanolamine, and p-chloromercury benzoate |
| Phosphatidyl transferase activity | Transfer to primary aliphatic, aromatic, alicyclic and heterocyclic alcohols having 1 to 26 carbon atoms, saccharides such as pentose and hexose, and some secondary alcohols is effected. | Same as the left. | Transfer to primary aliphatic alcohols having 1 to 6 carbon atoms is effected. No transfer to saccharides such as pentose and hexose and secondary alcohols. |
| Catalytic action on the formation of phospholipid-saccharide derivative between fructose and phospholipid (lecithin) | Yes | Yes | No |

Presumably, it is due to the aforesaid differences in enzymological properties between the known phospholipase D and the phosholipases DM used in the process of this invention that phospholipid-saccharide derivatives which cannot be obtained by using the known phospholipase D can be produced by the process of this invention. It should be understood however that this presumption does not in any way limit the process of this invention.

The microbiological properties of Nocardiopsis sp. No. 779 (FERM-P No. 6133; BP 512) and Actinomadura sp. No. 362 (FERM-P No. 6132; BP 511) which have the ability to produce phospholipase DM and can be utilized in the process of this invention, the method of measuring the potencies of the phospholipases DM produced by these microorganism strains and their physico-chemical properties are described below.

Microbiological properties of Nocardiopsis sp. No. 779 (FERM-P No. 6133; BP 512)

(a) Morphology

Growth good on glucose-asparagine-agar, glycerol-asparagine-agar, and yeast-malt-agar media, and moderate in a starch-inorganic salt-agar medium, forming colonies of aerial mycelia.

The color of the colonies having spores formed therein changes slightly with the type of the culture medium and the time of observation, but is generally white to grayish white to bright gray.

Aerial mycelia do not form, or grow poorly, on sucrose-nitrate-agar, nutrient agar and oatmeal-agar media.

Microscopic observation of this strain grown on an agar medium shows that the aerial hyphae are 0.5 to 0.8 micron in diameter and are long and straight with many branches, and sometimes gently wavy or flexuous. The entire aerial mycelia are formed of chains all composed of about 10 to 100 more more spores.

The spores are $0.5-0.8 \times 0.5 \times 1.6$ micron long, and nearly of a short cylindrical shape, and their sizes are slightly irregular.

Substrate hyphae are 0.4 to 0.7 micron in diameter, and stretch with branches. They do not always fragment on an agar medium, but when cultivated in a liquid culture medium, they fragment into small fragments in almost all cases.

Flagellated spores, sporangia, sclerotia, etc., are not formed, however.

(b) Characteristics on various media

The following experiments were carried out mainly in accordance with the methods of E. B. Shirling (Int. J. Syst. Bacteriol., vol. 16, pages 313–340, 1966).

The colors of the mycelia were determined by using "Standards of Colors" (Japanese Institute of Colors, 1964), and are described with a parenthesized symbolic or numerical indication of the color, saturation, and brightness in this order.

The cultivation was carried out at 25° C., and the results of observation on various media in the second to third weeks when the growth was most vigorous are summarized below. In the following description, the colors of the surfaces of substrate mycelia given under the headline "growth" are those observed after the lapse of one week from the initiation of cultivation which was before the formation of spores. No result is given where the evaluation of colors on the surfaces of substrate mycelia was difficult because of the early formation of spores.

Sucrose-nitrate-agar medium

Growth: Thin and poor. Colorless.
Color of substrate mycelium: Grayish white (19).
Aerial mycelium: Slightly formed. Colorless.
Soluble pigment: None.

Glucose-asparagine-agar medium

Growth: Good. Yellowish white (Y-1-19).
Color of substrate mycelium: Yellowish gray (rY-2-19).
Aerial mycelium: Abundant in cottony form. Light brownish gray (rO-1-17).
Soluble pigment: None.

Glycerol-asparagine-agar medium

Growth: Good.
Color of substrate mycelium: Pale yellow (rY-3-19).
Aerial mycelium: Formed thinly in cottony form. Light gray (18).
Soluble pigment: None.

Starch-inorganic salt-agar medium

Growth: Good. Yellowish gray (Y-1-19).
Color of substrate mycelium: Yellowish gray (rY-1-19).
Aerial mycelium: Moderate, powdery. Grayish white (19).
Soluble pigment: None.

Tyrosine-agar medium

Growth: Good. Yellowish brown (YO-3-16).
Color of substrate mycelium: Light brown (0-3-15).
Aerial mycelium: Good to excellent. Light gray (18).
Soluble pigment: Brown melanoid pigment produced.

Nutrient agar medium

Growth: Poor. Colorless.
Color of substrate mycelium: Brownish white (YO-1-19).
Aerial mycelium: Not formed.
Soluble pigment: None.

Yeast-malt-agar medium

Growth: Good.
Color of substrate mycelium: Dull yellow orange (YO-4-18).
Aerial mycelium: Good to excellent. Grayish white (19).
Soluble pigment: Brown melanoid pigment produced.

Oatmeal-agar medium

Growth: Moderate. Yellowish gray (Y-1-19).
Color of substrate mycelium: Yellowish gray (Y-1-19).
Aerial mycelium: Poor. White (20).
Soluble pigment: None.

(c) Physiological properties

1. Growth temperature
Grows at about 5° to 30° C., and best at 20° to 30° C.
2. Liquefaction of gelatin
Negative (when cultivated on a glucose-peptone-gelatin medium at 25° C. for 3 weeks).
3. Hydrolysis of starch
Positive (when cultivated on a starch-agar medium at 25° C. for 3 to 4 weeks).
4. Coagulation and peptonization of skimmed milk
Both negative (when cultivated at 30° C. for 3 to to 4 weeks).
5. Formation of a melanoid pigment
Positive on peptone-yeast-iron-agar and tyrosine-agar media (at 25° C. for 2 to 4 days).

(d) Utilization of carbon sources (when cultivated at 30° C. for 10 to 16 days)

L-arabinose: —
Sucrose: —
D-xylose: —
Inositol: —
D-glucose: +
L-rhamnose: —
D-fructose: —
Raffinose: —

(e) Chemical analysis of cells 2,6-Diaminopimelic acid of this strain has the meso-form of DAP in hydrolysates of whole organisms, and does not contain hydroxydiaminopimelic acid. The sugar pattern of the cell walls of this strain is such that it lacks arabinose, xylose, madurose, rhamnose, but contains galactose and mannose. The present strain does not contain nocardomycolic acid.

The foregoing analytical results are evaluated in accordance with the classification methods described in Bergey's Manual of the Determinative Bacteriology, 8th edition, pages 657–658 (1974), M. P. Lechevalier and H. A. Lechevalier, "Inter. J. System. Bacteriol., vol. 20, pages 435–443, 1970, and J. Meyer, Int. J. Syst. Bacteriol., vol. 26, pages 487–493, 1976. It was found that the cell wall type of the present strain is type III, and its cell wall sugar pattern is type C.

Because the present strain has cell wall type III and cell wall sugar pattern C, the Lechevalier's classification method shows it to belong to either of the genera Geodermatophilus, Actinobifida, Thermoactinomyces and Actinomadura of the dassonvillei type.

Since, however, the present strain has such morphological characteristics that all of the aerial mycelia are composed of long chains of spores, the substrate mycelia are finely fragmented, but no endospores, flagellated spores nor sporangia are found in it, it is reasonable to identify this strain as belonging to the genus Actimomadura of the dassonvilleic type. It is noted in this regard that the genus Actinomadura of the dassonvillei type has recently been unified into the new genus Nocardiopsis advocated by J. Meyer, and is generally dealt with by the name of genus Nocardiopsis.

Thus, the present strain was named Nocardiopsis sp. No. 779. It was deposited in Fermentation Research Institute of the Agency of Industrial Science and Technology, Japan under the deposit number "FERM-P No. 6133 (the international deposit number BP 512)".

In the present invention, not only Nocardiopsis sp. No. 779 and its mutant strains, but also all other strains belonging to the genus Nocardiopsis (the former genus Actinomadura of the dassonvillei type) and capable of producing phospholipase DM can be used to produce phospholipase DM.

Microbiological properties of Actinomadura sp. No. 362 (FERM-P No. 6132; the international deposit number BP 511)

(a) Morphology

Growth good on starch-inorganic salt-agar, tyrosine-agar, yeast-malt-agar, and oatmeal-agar media, but moderate on a glycerol-asparagine-agar medium, forming colonies of aerial mycelia.

The color of the colonies having spores formed therein varies slightly with the type of the culture medium and the time of observation, but generally it is slightly purplish grayish white to gray.

Aerial hyphae are not formed, or formed only poorly, on sucrose-nitrate-agar, nutrient agar and glucose-asparagine-agar media.

Microscopic observation of the present strain grown on an agar medium shows that the aerial mycelia are branched with a width of 0.7 to 0.8 microns, partly form loops or helical filaments, and are mainly straight with some flexuous parts, and their tips are mostly wound in loop form.

Spores are formed in 10 to 100 or more chains, and constitute almost the entire aerial mycelia.

The size of the spores is 0.7–0.8×0.7–1.6 microns, and their shape is short-cylindrical. Both their size and shape are slightly irregular.

The substrate mycelia are 0.4 to 0.7 micron wide, and stretch flexuously with irregular branches. No flagellated spores, sporangia nor sclerotia are formed.

Fragmentation of the septa and mycelia is not observed. (But sometimes, fragmentation of the mycelia occurs in liquid culture.)

(b) Characteristics on various culture media

The following experiments were carried out mainly in accordance with the methods of E. B. Shirling (Int. J. Syst. Bacteriol., vol. 16, pages 313–340, 1066).

The colors of mycelia were determined by using "Standards of Colors" (Japanese Institute of Colors, 1964), and are described with a parenthesized symbolic or numerical indication of the color, saturation, and brightness in this order.

The cultivation was carried out at 25° C., and the results of observation on various media in the second to third weeks when the growth was most vigorous are summarized below. In the following description, the colors of the surfaces of substrate mycelia given under the headline "growth" are those observed after one week from the initiation of cultivation which was before the formation of spores. No result is given where the evaluation of colors on the surfaces of substrate mycelia was difficult because of the early formation of spores.

Sucrose-nitrate-agar medium

Growth: Poor. Grayish white (19).
Color of substrate mycelium: Grayish white (19).
Aerial mycelium: Formed moderately in powder form. Grayish white (19).
Soluble pigment: None.

Glucose-asparagine-agar medium

Growth: Good. Yellowish white (Y-1-19).
Color of substrate mycelium: Light olive gray (Y-1-18).
Aerial mycelium: Formed poorly. Light brownish gray (YO-1-19).
Soluble pigment: None.

Glycerol-asparagine-agar medium

Growth: Moderate. Greenish white (gY-1-19).
Color of substrate mycelium: Pale yellowish brown (rY-2-18).
Aerial mycelium: Formed thickly in powder form. Light gray (18).
Soluble pigment: None.

Starch-inorganic salt-agar medium

Growth: Good. Yellowish gray (Y-1-19).
Color of substrate mycelium: Yellowish gray (Y-1-19).
Aerial mycelium: Good. Pale orange (0-2-19).
Soluble pigment: None.

Tyrosine-agar medium

Growth: Good. Pale yellowish brown (YO-2-18).
Color of substrate mycelium: Pale brown (YO-3-17).
Aerial mycelium: Good to excellent. Brownish white (0-1-19).
Soluble pigment: Brown melanoid pigment produced.

Nutrient agar medium

Growth: Thin and poor. Colorless.
Color of substrate mycelium: Brownish white (YO-1-19).
Aerial mycelium: Not formed.
Soluble pigment: Brown melanoid pigment produced.

Yeast-malt-agar medium

Growth: Good.
Color of substrate mycelium: Dull yellow (rY-4-18).
Aerial mycelium: Good to excellent. Light purplish gray (pR-1-17).
Soluble pigment: None.

Oatmeal-agar medium

Growth: Good. Yellowish gray (rY-1-19).
Color of substrate mycelium: Yellowish gray (rY-1-19).
Aerial mycelium: Good to excellent. Brownish white (YO-1-19).
Soluble pigment: None.

(c) Physiological properties

1. Growth temperature
Grows at about 10° to 37° C., and best at 20° to 30° C.
2. Liquefaction of gelatin
Negative (on a glucose-peptone-gelatin medium at 25° C. for 3 weeks).
3. Hydrolysis of starch
Positive (on a starch-agar medium at 25° C. for 3 weeks).
4. Coagulation and peptonization of skimmed milk Not coagulated but peptonized (at 30° C. for 3 to 4 weeks).

5. Formation of a melanoid pigment

Positive on peptone-yeast-iron-agar and tyrosine-agar media (at 25° C. for 2 to 4 days).

(d) Utilization of carbon sources (at 30° C. for 10 to 16 days)

L-arabinose: +
Sucrose: −
D-xylose: +
Inositol: ±
D-glucose: +
L-rhamnose: −
D-fructose: −
Raffinose: −

(e) Chemical analysis of cells 2,6-Diaminopimelic acid of this strain is of the meso-type. The sugar composition of the whole cell walls is such that it does not contain arabinose, xylose, rhamnose, but contains madurose, galactose and mannose.

The foregoing analytical results are evaluated in accordance with the classification methods described in Bergey's Manual of the Determinative Bacteriology, 8th edition, pages 657–658 (1974), and M. P. Lechevalier and H. A. Lechevalier, "Inter. J. System. Bacteriol., vol. 20, pages 435–443, 1970". It was found that the cell wall type of the present strain is type III, and its cell wall sugar pattern is type B.

Because the present strain has cell wall type III and cell wall sugar pattern B, it belongs to either of the genera Microbispora, Streptosporangium, Spirillospora, Planomonospora, Dermatophilus, and Actinomadura.

Since, however, the present strain has such morphological characteristics that spore chains composed of many spores are formed, and no sclerotia, flagellated spores nor sporangia are found in it, it is taxonomically reasonable to identify this strain as belonging to the genus Actimomadura.

Thus, the present strain was named Actinomadura sp. No. 362. It was deposited in Fermentation Research Institute of the Agency of Industrial Science and Technology, Japan under the deposit number "FERM-P No. 6132 (the international deposit number BP 511)".

In the present invention, not only Actinomadura sp. No. 362 and its mutant strains, but also all other strains belonging to the genus Actinomadura and capable of producing phospholipase DM can be used to produce phospholipase DM.

The phospholipase DM utilized in the process of this invention is produced by cultivating the phospholipase DM-producing strain exemplified above in a culture medium, and collecting phospholipase DM from the culture broth. The cultivation can be carried out in a liquid culture or solid culture mode, but industrially, a submerged culture mode is advantageous.

Carbon sources, nitrogen sources, inorganic salts and traces of other nutrients which are generally used in microbial cultivation may be used in this invention as cultivation sources. Other nutrient sources which phospholipase DM-producing microorganisms of the genus Nocardiopsis or Actinomadura can utilize may also be used in this invention.

Examples of the carbon sources include glucose, fructose, sucrose, lactose, starch, glycerol, dextrin, molasses, sorbitol, fatty acids, oils and fats, crude lecithin, alcohols and organic acids. They may be used either singly or in combination.

The nitrogen sources may be inorganic or organic. Examples of the inorganic nitrogen sources include ammonium nitrate, ammonium sulfate, urea, sodium nitrate, ammonium phosphate monobasic, ammonium phosphate dibasic and ammonium chloride. Examples of the organic nitrogen sources include flours, brans and oil extraction residues of soybean, rice, corn, cotton seed, rape seed and wheat, corn steep liquor, peptone, yeast extract, meat extract, casein and amino acids.

Examples of the inorganic salts and trace nutrients include salts of phosphoric acid, magnesium, potassium, iron, aluminum, calcium, manganese and zinc, vitamins, nonionic surface-active agents and defoamers. Such substances promote the growth of the microorganisms or the production of phospholipase DM, and may be used as required.

The cultivation is carried out under aerobic conditions. The cultivation may be properly selected and varied within a range of temperatures at which the microorganism strain grows well and produces phospholipase DM. Temperatures of about 20° to about 35° C. are especially preferred.

The cultivation time varies depending upon the cultivating conditions. The cultivation may be performed until the amount of the phospholipase DM produced reaches a maximum. In the case of liquid culture, for example, it is about 1 to 3 days.

The phospholipase DM produced in the culture broth is mainly dissolved in it. Hence, the phospholipase DM can be collected from the culture broth after removing solid materials from it by filtration.

In collecting the phospholipase DM from the filtrate, all methods usually employed for enzyme preparation can be utilized. The methods include, for example, salting out with ammonium sulfate, sodium chloride, etc., precipitation with organic solvents such as acetone, ethanol and methanol, dialysis, ion-exchange chromatography, adsorption chromatography, gel filtration, adsorption on adsorbents, and isoelectric precipitation. These methods may be combined if the combined use increases the effect of purifying phospholipase DM.

The phospholipase DM may be obtained in the form of a liquid or solid by, for example, adding various salts, sugars, proteins, lipids and surface-active agents as stabilizers, or by concentrating it under pressure, drying it under reduced pressure or lyophilizing it without adding such stabilizers.

The enzyme activity of the phospholipase DM utilized in the process of this invention is determined by measuring the amount of a base which is formed when the phospholipase DM acts on the substrate glycerophospholipid to decompose the ester linkage between phosphoric acid and the nitrogen-containing base. Unless otherwise indicated, the activity of phospholipase DM is measured by the choline oxidase method to be described hereinafter.

Method of measuring the activity of an enzyme

Distilled water (0.15 ml), 0.1 ml of 0.2M Tris-HCl buffer (pH 7.2) and 0.05 ml of 0.1M aqueous calcium chloride solution are mixed with 0.1 ml of 1% emulsion of purified lecithin from egg yolk (an emulsion of 0.1 g of lecithin, 1 ml of ethyl ether and 10 ml of distilled water obtained by ultrasonication). To the mixture is added 0.1 ml of an enzyme solution and reacted at 37° C. for 20 minutes. Then, 0.2 ml of 1M Tris-HCl buffer (pH 8.0) containing 50 mM disodium ethylenediamine tetraacetate, and immeidately then, the mixture is boiled for 5 minutes, followed by completely stopping the reaction. Then, 4 ml of a solution obtained by dissolving a choline color-forming agent contained in a kit of a reagent for choline esterase measurement (produced by Nippon Shoji Co., Ltd.) in a color dissolving liquid is added, and reacted at 37° C. for 20 minutes. Then, the absorbance of the reaction solution at 500 nm is measured.

As a control, the absorbance of the product obtained by the same procedure as above except that an enzyme solution previously deactivated by heat is used.

The activity of the enzyme to liberate 1 micromole of choline per minute is defined as one unit.

The physico-chemical properties of phospholipases DM produced and purified by the method shown below in section 9 (Method of purification) using Nocardiopsis sp. No. 779 and Actinomadura sp. No. 362 are described below.

1. Activity

These phospholipases DM decompose the ester linkage of phosphoric acid and a nitrogen-containing base in a glycerophospholipid to liberate the base and phosphatidic acid.

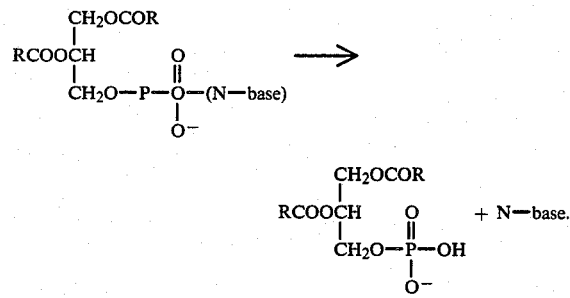

2. Substrate specificity

The same reaction as in the aforesaid method of measuring the activity of the enzyme was carried out except that 0.1 ml of an emulsion containing 0.5 micromole of each of lecithin, lysolecithin and sphingomyelin is used as a substrate and an aqueous solution containing 1% of Triton X-100 is used instead of distilled water. The amount of choline liberated as a result of the reaction is measured, and the activity of phospholipase DM on the substrate is measured. It was found that when the activity of the enzyme on lecithin is taken as 100, the relative activity of phospholipase DM derived from the Nocardiopsis strain is 4.9 on lysolecithin and 0.3 on sphingomyelin, and the relative activity of phospholipase DM derived from the Actinomadura strain is 3.6 on lysolecithin and 0.3 on sphingolyelin.

3. Optimum pH

The activity of phospholipase DM is measured by using a formic acid-sodium formate buffer at a pH of 3.0 to 4.0, an acetic acid-sodium acetate buffer at a pH of 4.0 to 5.5, a Tris-maleic acid-sodium hydroxide buffer at a pH of 5.5 to 8.5, a Tris-HCl buffer at a pH of 7.0 to 9.0, and a glycine-sodium hydroxide buffer at a pH of 9.0 to 10.0 instead of the buffer used in the method of measuring the activity of the enzyme. The optimum pH is thus measured. The optimum pH is also measured when 0.15 ml of a 1% aqueous solution of Triton X-100 (a reagent made by Wako Pure Chemicals Co., Ltd.) is used instead of 0.15 ml of distilled water.

It is found that when distilled water is used, the optimum pH of phospholipase DM from the Nocardiopsis strain is about 7 (6.5–7.0), and the optimum pH of phospholipase DM derived from the Actinomadura strain is about 7; and that when the 1% aqueous solution of Triton X-100 is used, the optimum pH of phospholipase DM derived from the Nocardiopsis strain is about 5, and the optimum pH of phospholipase DM derived from the Actinomadura strain is about 5.5.

4. Optimum temperature

The activity of the enzyme is measured by the method of measuring the activity of the enzyme at reaction temperatures of 10°, 20°, 25°, 37°, 40°, 50°, 60°, 70°, 80° and 90° C. The result is that the optimum temperature of phospholipase DM derived from the Nocardiopsis strain is 60° to 80° C., especially 60° to 70° C., and the optimum temperature of phospholipase DM derived from the Actinomadura strain is 55° to 80° C., especially 60° to 70° C.

5. pH stability

To 0.1 ml of an enzyme solution is added 0.2 ml (in the case of phospholipase DM derived from the Nocardiopsis strain) or 0.9 ml (in the case of phospholipase DM derived from the Actinomadura strain) of each of various buffers (0.1M). Specifically, there were used a glycine-HCl buffer at a pH of 3.0 to 3.5, an acetic acid-sodium acetate buffer at a pH of 3.5 to 7.0, a Tris-maleic acid-sodium hydroxide buffer at a pH of 5.0 to 8.0, a Tris-HCl buffer at a pH of 7.0 to 9.0, and a glycine-sodium hydroxide buffer at a pH of 9.0 to 9.5. The mixture is maintained at 25° C. for 2 hours. Thereafter, 1.2 ml (in the case of phospholipase DM derived from the Nocardiopsis strain), or 9.0 ml (in the case of phospholipase DM derived from the Actinomadura strain) of 0.5M Tris-HCl buffer (pH 7.2) is added to the resulting enzyme buffer solution to adjust its pH to 7.0 to 7.3. The activity of the enzyme is measured by using 0.1 ml of this solution in accordance with the method of measuring the activity of the enzyme described hereinabove. The stable pH range is thus examined. It is found that phospholipase DM derived from the Nocardiopsis strain is especially stable at a pH of 4.0 to 7.0, and phospholipase DM derived from the Actinomadura strain is especially stable at a pH of 4.0 to 8.0. The stable pH range is examined by the same procedure as above except that 0.15 ml of a 1% aqueous solution of Triton X-100 is used instead of 0.15 ml of distilled water used in the method of measuring the activity of the enzyme. The results are much the same as those obtained by the aforesaid procedure.

6. Heat stability

To 0.1 ml of an enzyme solution is added 4 ml (in the case of phospholipase DM derived from the Nocardiopsis strain) or 9.9 ml (in the case of phospholipase DM derived from the Actinomadura strain) of 0.1M Tris-HCl buffer (pH 7.2), and the mixture is left to stand for 30 minutes at a temperature of 20°, 30°, 37°, 40°, 50°, 60° and 65° C. respectively. The remaining enzyme activity is then measured. It is found consequently that the activity of phospholipase DM derived from the Nocardiopsis strain is scarcely lost by heat-treatment at 30° C. for 30 minutes, and and 80% of it remains after heat-treatment at 50° C. for 30 minutes and that the activity of phospholipase DM derived from the Actinomadura strain is scarcely lost by heat-treatment at 30° C. for 30 minutes, and 60% of it remains after heat-treatment at 50° C. for 30 minutes.

7. Influences of various substances

In the method of measuring the activity of the enzyme described hereinabove, 0.05 ml of an aqueous solution of each of various substances is added instead of the aqueous calcium chloride solution so that its concentration in the enzyme reaction system becomes 1 mM. The activity of the enzyme is then measured. The activity of the enzyme at the time of adding water is taken as 100, and the relative activity of the enzyme is determined. It is found that $AlCl_3$, $CuSO_4$, $ZnSO_4$, $CoCl_2$, $CaCl_2$, $FeCl_3$, $FeSO_4$, $MgCl_2$, $SnCl_2$, sodium deoxycholate, ethanol, isopropanol, t-butanol, and Triton X-100 have an activating action on phospholipase DM derived from the Nocardiopsis strain, and $AlC_3$, $CaCl_2$, $FeCl_3$, $FeSO_4$, $MgCl_2$, $SnCl_2$, sodium deoxycholate, ethanol, isopropanol, and t-butanol have an activating action on phospholipase DM derived from the Actinomadura strain. On the other hand, it is found that sodium dodecylsulfate and cetyl pyridinium chloride have an inhibiting action on phosphlipase DM derived from the Nocardiopsis strain, and acetyl pyridinium chloride has an inhibiting action on phospholipase DM derived from Actinomadura strain.

8. Method of measuring the activity of the enzyme (As stated hereinabove)

9. Method of Purification

About 15 liters of a culture medium (pH 6.0) composed of 3.0 g of soybean flour, 1.0% of corn steep liquor, 0.5 g of peptone, 0.1% of powdery yeast extract, 1.0 g of glucose, 0.25% of $NH_4NO_3$, 0.4% of $K_2HPO_4$, 0.01% of $MgSO_4.7H_2O$, and 0.1% of Tween-85 was put in a 30 liter jar fermentor, and sterilized at 120° C. for 15 minutes. Then, 1.5 liters of a seed culture was inoculated, and cultivated at 27° C. for 40 hours.

The seed culture had been prepared by putting 100 ml of an aqueous solution (pH 6.8) containing 1% of starch, 0.25% of $(NH_4)H_2PO_4$, 0.25% of peptone, 0.2% of $K_2HPO_3$ and 0.01% of $MgSO_4.7H_2O$ in a 500 ml Sakaguchi flask, sterilizing it with steam, inoculating one platinum loopful of spores of Nocardiopsis sp. No. 779 (PB 512) or Actinomadura sp. No. 362 (BP 511) into the culture medium, and cultivating it with shaking at 30° C. for 2 days at 120 rpm.

After the cultivation, solid materials of the cells were removed by centrifugation to obtain 13 liters of a supernatant liquid (0.54 u/ml in the case of using the Nocardiopsis strain; and 1.7 u/ml in the case of using the Actinomadura strain). The supernatant liquid was cooled to 5° C., and acetone kept at −20° C. was added. By centrifugation, precipitates containing phospholipase DM corresponding to fractions having an acetone concentration of 30 to 70% were collected. The precipitates were dissolved in Tris-maleic acid buffer (pH 6.0 in the case of using the Nocardiopsis strain, and pH 6.5 in the case of using the Actinomadura strain), dialyzed against the same buffer having a molarity of 0.02M, and passed through a DEAE-cellulose column equilibrated with the same buffer. Fractions which have passed through the column were collected. A palmitoyl gauze prepared by the method of Horiuti et al. [J. Biochem. 81, 1639 (1977)] was filled in a column. After washing the column fully with water, the collected fractions were charged onto the column to adsorp active components. The column was washed with 0.05M Tris-HCl buffer (pH 7.2) and then eluted with the same buffer containing 0.2% Triton X-100. Active fractions were collected and concentrated by using an ultrafiltration membrane (Type G-10T made by Bioengineering Co., Ltd.), then charged onto a column filled with Toyo-Pearl HW-55F (made by Toyo Soda Co., Ld.) as a gel fitration carrier, and passed through it by using distilled water. Active fractions were collected and lyophilized.

The dry powder was then dissolved in 0.025M imidazole-HCl (pH 7.4) (in the case of phospholipase DM derived from the Nocardiopsis strain), or 0.025M Tris-acetic acid (pH 8.3) (in the case of phospholipase DM derived from the Actinomadura strain). The solution was passed through a column filled with a polybuffer exchanger PBE$^{TN}$94 (20 ml) made by Pharmacia Fine Chemicals, Co. to adsorb active components. The column was then eluted by a pH gradient method using an eluting polybuffer made by the same company as above (pH 5.0). The eluted active fractions of phospholipase DM were collected and concentrated by an ultrafiltration membrane, and passed through a column filled with Sephadex G-75. Active fractions of phospholipase DM were collected and lyophilized.

As a result, phospholipase DM from the Nocardiopsis strain having a specific activity of 178.3 u/mg protein was recovered at an activity recovery ratio of about 40%. Furthermore, phospholipase DM from the Actinomadura strain having a specific activity of 218.3 u/mg protein was recovered at an activity recovery ratio of about 43%.

10. Isoelectric point

Phospholipase DM derived from the Nocardiopsis strain: 4.85 ±0.1 (measured by isoelectric focusing with Ampholine)

Phospholipase DM derived from the Actinomadura strain: 6.4 ±0.1 (measured by isoelectric focusing with Ampholine)

11. Transferring action

The conventional phospholipase D is known to produce phosphatidic acid from lecithin and transfers it to a linear primary alcohol having 1 to 5 carbon atoms to form an ester. But it has not been known that this enzyme induces formation of such an ester with a saccharide such as fructose. It has been found that the phospholipase DM used in accordance with this invention effects transfer to not only a broader range of alcohols, but also the aforesaid saccharides or their phenol glycosides to form esters.

The phospholipase DM used in the process of this invention catalyzes a reaction of forming a phospholipid-saccharide derivative between fructose and lecithin carried out in accordance with the method of experimenting the transfer action (the method of determining the formation of a transfer product by TLC) to be described hereinbelow to form the phospholipid-saccharide derivative. The known phospholipase D does not form the aforesaid derivative.

According to the process of this invention, a phospholipid-saccharide derivative can be produced by reacting the above-exemplified saccharide or its phenol glycoside with the phospholipid in the presence of the phospholipase DM described in detail hereinabove. At this time, the phospholipase DM needs not to be a pure product, and a crude product may also be used. It may also be immobilized to a suitable support, for example, a particulate or film-like carrier of various resins or inorganic materials such as a polypropylene film, Celite particles and glass beads.

The reaction can be carried out by contacting the phospholipid with the saccharide or its glycoside in the presence of the phospholipase DM, preferably in a solvent. The solvent may, for example, be an aqueous solvent or a mixture of an aqueous solvent and an organic solvent. Solvents containing additives which do not inhibit the enzymatic catalytic action of the phospholipase DM can also be utilized. They may be solvents containing suitable additives which serve to promote the enzymatic action of the enzyme or stabilize it. For example, they may be aqueous solvents containing buffers such as acetic acid, citric acid, or phosphoric acid, or neutral salts such as calcium chloride. Examples of the organic solvents include aliphatic hydrocarbons such as n-heptane and n-hexane; alicyclic hydrocarbons such as cyclopentane, cyclohexane and cyclobutane; aromatic hydrocarbons such as benzene, toluene and xylene; ketones such as acetone and methyl isopropyl ketone; ethers such as dimethyl ether, diethyl ether and diisopropyl ether; esters such as methyl acetate and ethyl acetate; halogenated hydrocarbons such as carbon tetrachloride, chloroform and methylene chloride: amides such as dimethylformamide; and sulfoxides such as dimethyl sulfoxide.

The mixing ratio of the aqueous solvent to the organic solvent may be properly selected, and is, for example, from 50:1 to 1:10 (V/V).

The molar proportions of the reactants, the amount of the phospholipase DM, the amount of the solvent, etc. may be properly chosen. For example, about 1 to about 1000 moles, preferably about 10 to about 1000 moles of the mono- or di-saccharide or its phenol glycoside may be used per mole of the phospholipid. The amount of the phospholipase DM is, for example, about 10 to about 100,000 units, preferably about 100 to 1,000 units per gram of phospholipid. The amount of the solvent is, for example, about 10 to about 500 times the volume of the phospholipid.

Since the reaction proceeds at room temperature, it is not particularly necessary to cool or heat the reaction system. As desired, however, it may be carried out under cooling or heating conditions. For example, the reaction temperature may be about 0° to about 90° C., preferably about 20° to about 60° C. The reaction time can also be properly selected, and may, for example, be about 1 minute to about 10 days, preferably about 0.1 to about 72 hours, more preferably about 1 to about 72 hours. If desired, the reaction may be monitored by utilizing such a technique as TLC (thin-layer chromatography), and by determining the formation of the desired product, the reaction time may be properly changed.

The phospholipid and the saccharides or its phenol glycoside can be contacted in the presence of the phospholipase DM in suitable modes. Usually, it is carried out under stirring or shaking conditions. When the phospholipase DM is utilized in the form of an immobilized enzyme on a suitable particulate or film-like carrier, it is possible to pass the reaction mixture through the immobilized enzyme film or immobilized enzyme particle layer by means of a circulating pump.

The phospholipid-saccharide derivative formed by performing the reaction as above can be used either as such or after it has been isolated in the form of a salt. The product may also be separated and purified by utilizing suitable known methods such as column chromatography on silica or alumina, high-performance liquid chromatography, countercurrent distribution, gel filtration, and adsorption chromatography.

The transfer of the phospholipid to the saccharide by the phospholipase DM occurs with saccharides having a primary alcohol group, such as glucose, galactose and mannose, but not with saccharides with the reduction of the 6-position and having no primary alcohol group such as fucose and rhamnose. Phospholipid-saccharide derivatives from glucose, galactose and mannose give only one spot in TLC separation. It has further been found that when glucose is treated with triphenyl chloromethane in pyridine to substitute triphenylmethane for the primary alcohol group, transfer of the phospholipid to the glucose does not take place. It is presumed from these facts that the transfer of the phospholipid to the saccharide by the phospholipase DM takes place at the site of the primary alcohol group of the saccharide.

According to the process of this invention, the phospholipid-saccharide derivative can be produced by reacting the phospholipid with the saccharide or its phenol glycoside in the presence of the phospholipase DM in the manner described hereinabove. The resulting phospholiplid-saccharide derivatives have excellent surface-activating action and exert great effects on the permeability of cell membranes. Accordingly, the phospholipid-saccharide derivatives of this invention are useful as a liposome-forming substrate, or as an emulsifier for cosmetics such as cream and lotion, fat solutions for transfusion, and agricultural chemicals such as pesticides and herbicides.

Furthermore, in many cases, phospholipids are known to have unique physiological properties. Since many of the derivatives obtained by the process of this invention have a similar structure to the phospholipids, they are expected to exhibit various biological activities. Furthermore, the derivatives of this invention are useful as intermediates for synthesis of chemicals including various medicines. A labelled phospholipid derivative may be obtained by transferring a saccharide labelled with tritium or $^{14}C$, and can be utilized for elucidating the metabolic pathways of phospholipids.

The following examples illustrate the process of this invention in greater detail.

REFERENTIAL EXAMPLE 1

Preparation of phospholipases DM

In accordance with the Method of Purification in section (9) above, phospholipases DM were obtained in the activity recovery ratios and specific activities described in the aforesaid section using Nocardiopsis sp. No. 779 (FERM-P No. 6133; BP 512) and Actinomadura sp. No .362 (FERM-P No. 6132: BP 511).

EXAMPLE 1 (RUNS NOS. 1 TO 43)

The following phospholipids were respectively reacted with the various saccharides shown in Table 2 below in the presence of the phospholipases DM in accordance with the method of determining the formation of transfer products (phospholipids-saccharides) by TLC. The Rf values of the products are given in Table 2.

Substrate I: L-alpha-lecithin, beta,gamma-dimirystoyl (Sigma Co.)(1,2-ditetradecanoyl-Sn-glycerol-3-phosphorylcholine)

Substrate II: L-alpha-lecithin, beta,gamma-dihexadecyl (Calbiochem-Behring Co.) (1,2-dihexa-decyl-Sn-glycerol-3-phophorylcholine)

Substrate III: (L-alpha-lecithin, beta,gamma-hexadecylidine (ditto) (1,2-cyclohexadecylidene-Sn-gycerol-3-phosphorylcholine)

Method of determining the formation of the transfer product by TLC:

0.1 ml (0.2 - 1.0 u/0.1 ml) of an aqueous solution of the phospholipase DM was added to a reaction solution having the following formulation.

| | |
|---|---|
| 1% phospholipid emulsion | 0.1 ml |
| 0.4 M acetate buffer (pH 5.7) | 0.1 ml |
| 0.1 M aqueous calcium chloride solution | 0.05 ml |
| Distilled water | 0.1 ml |
| 10% saccharide solution | 0.1 ml |

The mixture was left to stand at 37° C. for 1 to 5 hours.

The 1% phospholipid emulsion was prepared by adding 1 ml of diethyl ether and 10 ml of distilled water to 100 mg of the phospholipid, and subjecting the mixture to ultrasonication for 5 minutes with ice cooling at 600 W and 20 KHz.

After standing, 0.2 ml of a 50 mM aqueous solution of EDTA was added, and 5 ml of a mixture of chloroform and methanol (2:1 by volume) was added. The mixture was vigorously stirred to extract a lipid (product). The resulting suspension was centrifuged for 10 minutes at 2000 ×g. The lower chloroform layer was separated, dried under reduced pressure at 30° C., and dissolved in 75 microliters of a mixture of chloroform and methanol (1:1 by volume) to form a sample for TLC. Ten microliters of the sample was spotted on a thin layer of silica gel (Funagel 60 Å, 20 cm×20 cm, a product of Funakoshi Yakuhin K.K.), and the silica gel layer was developed with a mixture of diisobutyl ketone, acetic acid and water (40:25:5). The following reagents were used for detecting the spots. When a spot of a phospholipid other than those of the undecomposed substrate and its hydrolysis products (phosphatidic acid and its analogs) was detected, it was determined to be the transfer product.

Detecting reagents

Color formation of phosphoric acid: Zinzade's reagent (Beiss. U, J. Chromatog., 13, 104, 1964)

Color formation of saccharide: Naphthoresorcinol-phosphoric acid reagent (G. W. Hag et al. J. Chromatog., 11, 479, 1963)

Color formation of amino sugar: Acetylacetone-Ehrlich reagent (Elson-Morgan reaction; S. M. Partridge, Biochem. J., 42, 238, 1948).

COMPARATIVE EXAMPLE 1

The procedure of Example 1 as repeated except that known phospholipase D derived from cabbage (P-L Biochemicals, Inc.) was used instead of the phospholipase DM in Example 1. It was found that with this known phospholipase, no transfer products were obtained with the saccharides indicated in Table 2 below.

TABLE 2

| Run No. | Saccharide added | | Rf value of the transfer product | | |
|---|---|---|---|---|---|
| | | | Substrate I | Substrate II | Substrate III |
| | Not added | Phosphatidic acid | 0.59 | 0.49 | 0.44 |
| | | Substrate | 0.27 | 0.25 | 0.20 |
| 1 | L-arabinose | | 0.36 | 0.29 | 0.27 |
| 2 | D-ribose | | 0.35 | 0.29 | 0.28 |
| 3 | D-xylose | | 0.35 | 0.31 | 0.28 |
| 4 | D-2-deoxyglucose | | 0.32 | 0.30 | 0.27 |
| 5 | D-glucose | | 0.32 | 0.28 | 0.30 |
| 6 | D-galactose | | 0.34 | 0.28 | 0.28 |

TABLE 2-continued

| Run No. | Saccharide added | Substrate I | Substrate II | Substrate III |
|---|---|---|---|---|
| 7 | D-mannose | 0.32 | 0.30 | 0.28 |
| 8 | D-fructose | 0.34 | 0.30 | 0.27 |
| 9 | L-sorbose | 0.34 | 0.30 | 0.27 |
| 10 | D-glucosamine* | 0.30 | 0.28 | 0.24 |
| 11 | D-mannosamine" | 0.32 | 0.28 | 0.26 |
| 12 | D-galactosamine" | 0.32 | 0.28 | 0.24 |
| 13 | N—acetyl-D-glucosamine* | 0.37 | 0.32 | 0.27 |
| 14 | N—acetyl-D-mannosamine* | 0.37 | 0.32 | 0.25 |
| 15 | N—acetyl-D-galactosamine" | 0.36 | 0.32 | 0.25 |
| 16 | Arbutin | 0.50 | 0.42 | 0.38 |
| 17 | Salicin | 0.48 | 0.42 | 0.38 |
| 18 | Saccharose | 0.29 | 0.27 | 0.22 |
| 19 | Maltose | 0.29 | 0.28 | 0.22 |
| 20 | D-alpha-glucoheptose | 0.32 | 0.29 | 0.27 |
| 21 | Sedoheptulose | 0.31 | 0.29 | 0.26 |
| 22 | Lactose | 0.20 | 0.19 | 0.17 |
| 23 | Cellobiose | 0.19 | 0.17 | 0.16 |
| 24 | Gentiobiose | 0.18 | 0.16 | 0.15 |
| 25 | Melibiose | 0.18 | 0.16 | 0.15 |
| 26 | Isomaltose | 0.18 | 0.16 | 0.15 |
| 27 | alpha-Methyl-glucoside | 0.33 | 0.31 | 0.29 |
| 28 | beta-Methyl-glucoside | 0.32 | 0.30 | 0.28 |
| 29 | 3-0-Methyl-glucose | 0.33 | 0.31 | 0.28 |
| 30 | 1-o-Phenyl-alpha-D-glucoside | 0.38 | 0.33 | 0.30 |
| 31 | 1-o-Phenyl-beta-D-glucoside | 0.37 | 0.33 | 0.30 |
| 32 | alpha-Methyl-mannoside | 0.33 | 0.31 | 0.28 |
| 33 | beta-Methyl-mannoside | 0.32 | 0.30 | 0.29 |
| 34 | alpha-Methyl-galactoside | 0.33 | 0.30 | 0.28 |
| 35 | beta-Methyl-galactoside | 0.32 | 0.30 | 0.28 |
| 36 | 1-o-Phenyl-alpha-D-galactoside | 0.38 | 0.33 | 0.30 |
| 37 | 1-o-Phenyl-beta-D-galactoside | 0.37 | 0.32 | 0.29 |
| 38 | alpha-Methyl-xyloside | 0.33 | 0.30 | 0.27 |
| 39 | beta-Methyl-xyloside | 0.32 | 0.29 | 0.26 |
| 40 | beta-Methyl-riboside | 0.33 | 0.28 | 0.25 |
| 41 | 2-o-Methyl-D-xylose | 0.33 | 0.30 | 0.28 |
| 42 | beta-Methyl-D-arabinoside | 0.32 | 0.30 | 0.28 |
| 43 | beta-Methyl-L-arabinoside | 0.34 | 0.31 | 0.29 |

(Note) Products from the nonmarked saccharides were detected by the Zinzade's reagent and naphthoresorcinol-phosphoric acid reagent; and products from the asterisked saccharides, by the Zinzade's reagent and the acetylacetone-Ehrlich reagent.

EXAMPLE 2 (RUNS NOS. 1 TO 8)

Four hundred milligrams of L-alpha-lecithin, beta, gamma-dimyristoyl (a product of Sigma Chemical Co.; purity 98%), 1 ml of diethyl ether and 10 ml of distilled water were put in a cell for ultrasonication, and with ice cooling, subjected to an ultrasonication treatment for 5 minutes at 600 W and 20 KHz to give a milk-white emulsion.

Two milliliters of the lecithin emulsion (80 mg of lecithin), 2 ml of a 0.4M acetate buffer (pH 5.7), 1 ml of a 0.1M aqueous solution of calcium chloride and 2 ml of a 10% aqueous solution of D-glucosamine hydrochloride were put in a test tube with a ground stopper. Then, 2 ml of an aqueous solution of phospholipase DM (8 u/ml) was added and well mixed. The mixture was left to stand at 37° C. for 4 hours. To the reaction mixture was added 0.5 ml of 0.5N hydrochloric acid to stop the reaction, and 15 ml of a mixture of chloroform and methanol (2:1 by volume) was further added. They were vigorously shaken to extract the phospholipid. The mixture was centrifuged for 10 minutes at 2,000 ×g, and the lower chloroform layer was separated.

Chloroform (10 ml) was again added to the upper aqueous layer and the same extracting operations was carried out. The extracts were combined and then washed with 10 ml of 0.02N hydrochloric acid. By centrifugation, the chloroform layer was again separated from this mixture, dried under reduced pressure, and dissolved in 1 ml of a mixture of n-hexane, 2-propanol and water (60:80:7).

Twenty microliters of this sample was spotted on a thin layer of silica gel (Funagel, a product of Funakoshi Yakuhin K.K.), and the silica gel layer was developed with a solvent system composed of diisobutyl ketone, acetic acid and water (40:25:5). Three phospholipids were detected, and two of them agreed in Rf values with phosphatidic acid and lecithin. The remaining one spot was subjected to color reaction with the ninhydrin reagent and acetylacetone-Ehrlich reagent.

This sample was purified by high-performance liquid chromatography. The column used was a Radial-Pak cartridge silica, 8 mm×10 cm, (made by Waters Co.), and the eluent used was a mixture of n-hexane, 2-propanol and water (60:80:7). The flow rate was 2 ml/min. For detecting peaks, a 441-type ultraviolet detector (made by Waters Co.) for determining an absorption at 214 nm and a R401-type differential refractometer (made by Waters Co.) were used. The sample was injected into the column four times in an amount of 0.25 ml each time. By this procedure, phosphatidic acid and a glucosamine ester of phosphatidic acid were fractionated. Then, the lecithin adsorbed on the column was eluted with n-hexane-2-propanol-water (60:80:14) as an eluent. The three phospholipids were each determined to be a single entity by thin-layer chromatography and high-performance liquid chromatography.

The proportions of the three phospholipids were as follows:
Phosphatidic acid: about 40%
Transfer product: about 20%
Lecithin: about 40%

Thus, about 12 mg of phosphatidic acid-glucosamine ester was obtained. The IR spectrum of this compound was measured by using an infrared spectrophotometer (Model A202 made by Nippon Bunko K.K.). The results are shown in Table 3 (Run No. 3).

The above procedure was repeated by using the other saccharides shown in Table 3. The results are shown in Table 3 (Runs Nos. 1 to 2 and 4 to 8).

TABLE 3

Infrared spectra of the transfer products between 1,2-ditetradecanoyl-Sn—glycerol-3-phosphoric acid and various saccharides

| Run No. | Saccharide as an acceptor in a transfer reaction | IR $\nu_{max}$ |
|---|---|---|
| 1 | D-ribose | 3300, 2930, 2860, 1740, 1470, 1380, 1230, 1175, 1110, 1070, 950, 840, 720 |
| 2 | D-fructose | 3350, 2930, 2860, 1740, 1460, 1380, 1230, 1175, 1100, 1060, 990, 850, 720 |
| 3 | D-glucosamine | 3250, 2920, 2850, 1735, 1625, 1535, 1465, 1375, 1205, 1180, 1090, 1050, 830, 720 |
| 4 | N—acetyl-D-glucosamine | 3300, 2930, 2860, 1740, 1640, 1555, 1470, 1380, 1235, 1175, 1100, 1060, 850, 720 |
| 5 | Arbutin | 3350, 2920, 2850, 1740, 1500, 1465, 1380, 1220, 1175, 1100, 1070, 1000, 880, 825, 720 |
| 6 | Saccharose | 3300, 2920, 2850, 1735, 1465, 1380, 1230, 1200, 1170, 1100, 1065, 990, 920, 860, 720 |
| 7 | beta-Methyl-glucoside | 3350, 2940, 2850. 1740, 1460, 1375, 1240, 1160, 1025, 860, 720 |
| 8 | alpha-Methyl-glucoside | 3350, 2940, 2830, 1740, 1450, 1380, 1240, 1160, 1030, 910, 840, 770, 720 |

EXAMPLE 3 (RUNS NOS. 1 TO 6)

A mixture of 400 mg of L-alpha-lecithin, beta, gamma-dihexadcyl (a product of Calbiochem-Behring Co.), 1 ml of diethyl ether and 10 ml of distilled water was emulsified in the same way as in Example 2. Thereafter, the same reaction as in Example 2 was carried out except that a 10% aqueous solution of ribose was used as the saccharide.

The reaction mixture was worked up in the same way as in Example 2 to give 10 mg of a transfer product. The IR spectrum of this product is shown in Table 4 (Run No. 1).

The above procedure was repeated using the other saccharides shown in Table 4. The results are shown in Table 4 (Runs Nos. 2 to 6).

TABLE 4

Infrared spectra of the transfer products between 1,2-dihexadecyl-Sn—glycerol-3-phosphoric acid and various saccharides

| Run No. | Saccharide as an acceptor in a transfer reaction | IR $\nu_{max}$ |
|---|---|---|
| 1 | D-ribose | 3300, 2920, 2850, 1465, 1380, 1220, 1110, 1045, 960, 865, 720 |
| 2 | D-fructose | 3300, 2930, 2860, 1470, 1380, 1230, 1205, 1095, 1050, 990, 860, 720 |
| 3 | D-glucosamine | 3280, 2920, 2850, 1620, 1530, 1465, 1380, 1215, 1090, 1020, 980, 945, 840, 720 |
| 4 | N—acetyl-D-glucosamine | 3300, 2930, 2800, 1650, 1555, 1470, 1380, 1235, 1205, 1100, 1050, 970, 875, 720 |
| 5 | Arbutin | 3320, 2920, 2850, 1500, 1465, 1380, 1215, 1095, 1065, 995, 880, 830, 720 |
| 6 | Saccharose | 3300, 2920, 2850, 1465, 1380, 1230, 1205, 1100, 1050, 990, 910, 860, 720 |

EXAMPLE 4 (RUNS NOS. 1 TO 6)

Four hundred milligrams of L-alpha-lecithin beta, gamma-hexadecylidine (a product of Calbiochem-Behring Co.) was emulsified in the same way as in Example 2. The same reaction, extraction and purification as in Example 2 were carried out using the emulsion (containing 80 mg of the phospholipid) and fructose as an acceptor in the transfer reaction. As a result, 12 mg of the transfer product was obtained. The IR spectrum of the product is shown in Table 5 (Run No. 2).

The above procedure was repeated using the other saccharides shown in Table 5. The results are shown in Table 5 (Runs Nos. 1 and 3 to 6).

TABLE 5

Infrared spectra of the transfer products between 1,2-cyclohexanedecylidene-Sn—glycerol-3-phosphoric acid and various saccharides

| Run No. | Saccharide as an acceptor in a transfer reaction | IR $\nu_{max}$ |
|---|---|---|
| 1 | D-ribose | 3300, 2920, 2850, 1465, 1380, 1225, 1105, 1050, 990, 840, 720 |
| 2 | D-fructose | 3300, 2920, 2850, 1465, 1380, 1230, 1100, 1040, 985, 850, 720 |
| 3 | D-glucosamine | 3260, 2920, 2850, 1625, 1530, 1465, 1380, 1220, 1090, 1040, 985, 850, 720 |
| 4 | N—acetyl-D-glucos-amine | 3300, 2930, 2860, 1645, 1555, 1465, 1380, 1230, 1100, 1050, 970, 850, 720 |
| 5 | Arbutin | 3300, 2920, 2850, 1500, 1465, 1380, 1220, 1095, 1065, 995, 880, 840, 720 |
| 6 | Saccharose | 3300, 2920, 2850, 1465, 1380, 1225, 1200, 1105, 1065, 990, 920, 860, 720 |

EXAMPLE 5 (RUN NOS. 1 TO 5)

Each of L-alpha-phosphatidyl ethanolamine, beta, gamma-dimyristoyl (I), L-alpha-phosphatidyl N-methyl ethanolamine, beta, gamma-dimyristoyl (II), L-alpha-phosphatidyl-DL-glycerol beta, gamma-dimyristoyl (III) (the above three compounds are products of Calbiochem-Behring Co.), L-alpha-phosphatidyl serine (IV) (a product of Sigma Co.), and L-alpha-phosphatidyl ethanol, beta, gamma-dimyristoyl (V) prepared by the method of S. F. Yang, et cl. (J. Biol. Chem., 242, 477, 1967) was emulsified by the same method as in Example 2. Emulsions (1.5 ml) containing 50 mg of the individual phospholipids were put into separate test tubes with a ground stopper. One milliliter of a 10% aqueous solution of ribose as the saccharide, 1 ml of 0.4M acetate buffer, 1 ml of distilled water and 0.5 ml of a 0.01M aqueous solution of calcium chloride were added, and the mixture was subjected to an ultrasonication treatment for 1 minute at 600 W and 20 KHz. One milliliter of an aqueous solution of phospholipase DM (8 u/ml) was added to each of the reaction solutions, and the mixture was left to stand at 37° C. for 6 hours. The extraction and purification of the phospholipids were carried out in the same way as in Example 2 to give a ribose ester of phosphatidic acid as a common transfer product. The amount of the product yielded was 9 mg for I, 6 mg for II, 9 ml for III, 4 mg for IV and 6 mg for V.

The IR spectrum of the product is shown in Table 6.

TABLE 6

| Run No. | Phospholipid | IR $\nu_{max}$ |
|---|---|---|
| 1 | I | 3300, 2920, 2850, 1740, 1465, 1380, 1230, 1175, 1100, 1070, 950, 840, 720 |
| 2 | II | 3300, 2920, 2850, 1740, 1465, 1380, 1230, 1175, 1100, 1070, 950, 840, 720 |
| 3 | III | 3300, 2920, 2850, 1740, 1465, 1380, 1230, 1175, 1100, 1070, 950, 840, 720 |
| 4 | IV | 3300, 2920, 2850, 1740, 1465, 1380, 1230, 1175, 1100, 1070, 950, 840, 720 |
| 5 | V | 3300, 2920, 2850, 1740, 1465, 1380, 1230, 1175, 1100, 1070, 950, 840, 720 |

What we claim is:

1. A process for producing a saccharide derivative of a phospholipid, which comprises reacting a phospholipid represented by the following formula

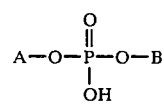

wherein
A is a moiety represented by the following formula (i)

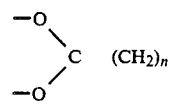

in which $R_1$ and $R_2$ both represent —O—COR$_{11}$ or —O—R$_{12}$, or $R_1$ and $R_2$ in formula (i) together represent

in which n represents a number of from 11 to 19, and R$_{11}$ and R$_{12}$ are identical or different and each represents a saturated or unsaturated aliphatic hydrocarbon group having 7 to 21 carbon atoms, and
B represents the group —CH$_2$)$_2$N$^+$(CH$_3$)$_3$, —CH$_2$)$_2$NH$_2$, —CH$_2$CH(NH$_2$)COOH, —CH$_2$CH$_2$NH(CH$_3$), —CH$_2$CH$_2$N(CH$_3$)$_2$, —CH$_2$CHOHCH$_2$OH or —CH$_2$)$_m$H in which m represents a number of from 1 to 5, with a monosaccharide having 5 to 7 carbon atoms, at least one primary alcohol group and at least three hydroxyl groups in total including the OH of the at least one primary alcohol group or a disaccharide thereof, said saccharide being unsubstituted or substituted by a group selected from the class consisting of amino and acetylamino groups, or a phenol glycoside of said saccharide in the presence of phospholipase DM.

2. The process of claim 1 wherein the phospholipid is at least one member selected from the group consisting of lecithin, cephalin, phosphatidyl serine, phosphatidyl N-methylethanolamine, phosphatidyl glycerol, phosphatidyl N,N-dimethylethanolamine and alkyl esters of phosphatidic acid.

3. The process of claim 1 wherein the mono- or disaccharide or its phenol glycoside is selected from the group consisting of D- and L-arabinoses, D-ribose, 2-deoxy-D-ribose, D-lyxose, D-xylose, D- and L-ribuloses, D- and L-xyluloses, 2-deoxy-D-glucose, D-glucose, D-galactose, D-mannose, L-sorbose, D-talose, D-fructose, D-alpha-glucoheptose, sedoheptulose, alpha- or beta-methyl-galactoside, alpha- or beta-methyl-glucoside, alpha- or beta-methyl-mannoside, alpha- or beta-methyl-xyloside, beta-methyl-arabinoside, 3-O-methyl-glucose, 2-O-methyl-xylose, beta-methyl-riboside, D-galactosamine, D-glucosamine, D-mannosamine, N-acetyl-D-galactosamine, N-acetyl-D-glucosamine, N-acetyl-D-mannosamine, salicin, arbutin, 1-o-phenyl-alpha-D-glucoside, 1-o-phenyl-beta-D-glucoside, 1-o-phenyl-alpha-D-galactoside, 1-o-phenyl-beta-D-galactoside, saccharose, maltose, cellobiose, gentiobiose, lactose, melibiose and isomaltose and N,N'-diacetylchitobiose.

4. The process of claim 1 wherein the reaction is carried out by contacting the phospholipid and the mono- or di-saccharide in the presence of the phospholipase DM at a temperature of about 0° to about 90° C.

5. A phospholipid-saccharide derivative produced by the process of claim 1.

6. The phospholipid-saccharide derivative according to claim 5 wherein the phospholipid is at least one member selected from the group consisting of lecithin, cephalin, phosphatidyl serine, phosphatidyl N-methylethanolamine, phosphatidyl glycerol, phosphatidyl N,N-dimethylethanolamine and alkyl esters of phosphatidic acid, and wherein the mono- or di-saccharide or its phenol glycoside is selected from the group consisting of D- and L-arabinoses, D-ribose, 2-deoxy-D-ribose, D-lyxose, D-xylose, D- and L-ribuloses, D- and L-xyluloses, 2-deoxy-D-glucose, D-glucose, D-galactose, D-mannose, L-sorbose, D-talose, D-fructose, D-alpha-glucoheptulose, sedoheptulose, alpha- or beta-methyl-galactoside, alpha- or beta-methyl-glucoside, alpha- or beta-methyl-mannoside, alpha- or beta-methyl-xyloside, beta-methyl-arabinoside, 3-O-methyl-glucose, 2-O-methyl-xylose, beta-methyl-riboside, D-galactosamine, D-glucosamine, D-mannosamine, N-acetyl-D-galactosamine, N-acetyl-D-glucosamine, N-acetyl-D-mannosamine, salicin, arbutin, 1-o-phenyl-alpha-D-glucoside, 1-o-phenyl-beta-D-glucoside, 1-o-phenyl-alpha-D-galactoside, 1-o-phenyl-beta-D-galactoside, saccharose, maltose, cellobiose, gentiobiose, lactose, melibiose, isomaltose and N,N'-diacetylchitobiose.

7. The process of claim 1 wherein the phospholipase DM is derived from a microorganism belonging to the genus Nocardiopsis.

8. The process of claim 1 wherein the phospholipase DM is derived from a microorganism belonging to the genus Actinomadura.

9. The process of claim 4 wherein the reaction is carried out by contacting the phospholipid with the saccharide or its glycoside in the presence of the phospholipase DM in an aqueous solvent or in a mixture of an aqueous solvent and an organic solvent.

10. The process of claim 1 wherein from about 1 to about 1,000 moles of the mono- or di-saccharide or its phenol glycoside is used per mole of the phospholipid.

11. The process of claim 1 wherein the amount of the phospholipase DM is from about 10 to about 100,000 units per gram of phospholipid.

12. The process of claim 1 wherein from about 10 to about 1,000 moles of the mono- or di-saccharide or its phenol glycoside is reacted per mole of the phospholipid in the presence of from about 100 to 1,000 units of phospholipase DM per gram of phospholipid.

13. The process of claim 12 wherein the reaction is carried out in a solvent in an amount of from about 10 to about 500 volumes of solvent per volume of phospholipid.

14. The process of claim 13 wherein the reaction is carried out at a reaction temperature of from about 20° to 60° C.

15. The process of claim 1 wherein the phospholipase DM is immobilized on a particulate or a film-like carrier.

* * * * *